United States Patent [19]

Foster

[11] 4,353,361

[45] Oct. 12, 1982

[54] ORTHOTIC/PROSTHETIC JOINT

[76] Inventor: Robert W. Foster, 16B Dayton Ct., Newington, Conn. 06111

[21] Appl. No.: 181,119

[22] Filed: Aug. 25, 1980

[51] Int. Cl.$^3$ .............................................. A61F 5/00
[52] U.S. Cl. ....................................... 128/80 C; 3/22; 128/80 F; 128/88; 2/22; 403/62; 403/113; 403/117
[58] Field of Search ...................... 3/22, 2, 1.91, 1.911; 128/80 C, 80 F, 80 R, 88; 2/24, 22; 403/62, 113, 117

[56] References Cited

U.S. PATENT DOCUMENTS

| | | | |
|---|---|---|---|
| 552,143 | 12/1895 | Rankin | 128/88 |
| 3,825,357 | 7/1974 | Hilton | 3/22 X |
| 4,193,139 | 3/1980 | Walker | 3/1.91 |

FOREIGN PATENT DOCUMENTS

| | | | |
|---|---|---|---|
| 473487 | 3/1929 | Fed. Rep. of Germany | 3/22 |
| 1008446 | 5/1957 | Fed. Rep. of Germany | 3/22 |

OTHER PUBLICATIONS

"The Genucentric Knee Orthosis-A New Concept" by Robert Foster et al., Orthotics and Prosthetics, vol. 33, No. 2, pp. 31-44, Jun. 1979.

*Primary Examiner*—Ronald L. Frinks
*Attorney, Agent, or Firm*—McCormick, Paulding & Huber

[57] ABSTRACT

An articulated orthotic/prosthetic appliance for supporting an infirm anatomical knee includes joint assemblies which prevents abnormal or injurious knee motion while freely permitting normal or desirable motion. The appliance includes upper and lower support members having associated spaced apart end portions which form parts of the joint assemblies. Each joint includes a generally disc shaped connecting member disposed intermediate associated end portions of upper and lower support members. The end portions are secured to the connecting member for independent pivotal movement about parallel axes. Concealed stops carried by and disposed intermediate the end portions cooperate with the connecting member to limit pivotal movement of the support members relative to each other.

14 Claims, 10 Drawing Figures

ORTHOTIC/PROSTHETIC JOINT

BACKGROUND OF THE INVENTION

This invention relates in general to articulated orthotic and prosthetic appliances, and deals more particularly with improved joint assemblies for such appliances. The joint assemblies of the present invention are suitable for use in orthotic and prosthetic appliances for treating various afflictions and particularly the infirmities known as: genu recurvatum, genu valgum, and genu varum. Genu recurvatum is characterized by the overextending of the knee joint resulting in a limb that bends backwards, from normal at the knee. Genu valgum is an abnormality characterized by a laterally inward bending of the knee, that is an inward bending toward the other knee, whereas genu varum is characterized by a laterally outward bending of the knee from its normal position of orientation.

Heretofore, articulated orthotic and prosthetic appliances have been provided for use in connection with the aforesaid afflictions. Such an appliance is illustrated and described in an article entitled "The Genucentric Knee Orthosis—A New Concept", published in the Journal of the American Orthotic and Prosthetic Association, June 1979, Volume 33, Number 2, coauthored by applicant. The knee orthosis illustrated and described in the aforesaid article includes upper and lower limb support members joined by a connecting member and arranged for independent pivotal movement about parallel axes to provide instantaneous centers of rotation which closely conform to those of the anatomical knee supported by the appliance. Further, the joint assemblies of the aforedescribed prior art structure are provided with stops for limiting pivotal movement of the upper and lower support members relative to each other to prevent overextension of the knee joint or other undesirable knee motion. However, these stops are exposed externally of the joint assemblies and present pinch points which may be fouled by the wearer's clothing. Further, the construction of these joints is such that the upper support members which form parts of the joints must necessarily be disposed at the inner sides of the joints, that is the sides adjacent the wearer's leg. This arrangement is most disadvantageous in a prosthetic application where a wall of the socket, due to the necessity for intimate fit with the residual limb, forms a portion of the joint or must be in close proximity to the lower portion of the joint. The present invention is concerned with the aforedescribed problems.

SUMMARY OF THE INVENTION

In accordance with the present invention an improved orthotic/prosthetic joint assembly includes elongated first and second support members and a connecting member disposed intermediate the support members, first connecting means securing the first support member to the connecting member for pivotal movement about a first axis in one direction from a first position, second connecting means securing the second support member to the connecting member for pivotal movement of the second support member about a second axis parallel to the first axis and in a direction opposite the one direction from the first position, first stop means disposed intermediate the end portions for preventing pivotal movement of the first support member in the other direction from the first position, and second stop means disposed intermediate the end portions for preventing pivotal movement of the second support member in its one direction from the first position.

BRIEF DESCRIPTION OF PREFERRED EMBODIMENTS

Figure 1:
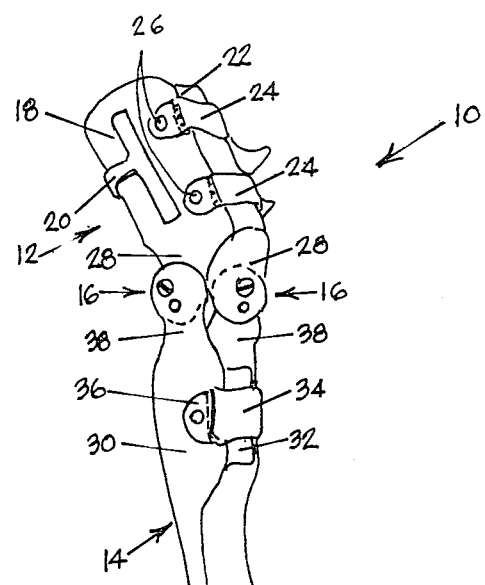
FIG. 1 is a perspective view of a limb orthosis for supporting an infirm knee and having joint assemblies embodying the invention.

Referring now to the drawings, an orthotic appliance embodying the present invention is shown in FIG. 1 and designated generally by the numeral 10. The appliance 10 is particularly suitable for utilization in connection with the infirmities known as genu recurvatum, genu valgum and genu varum and includes upper and lower limb supports indicated generally at 12 and 14, respectively, and connecting joint assemblies designated generally by the numerals 16, 16. Each limb support includes an intimately fitting cuff and support members connected to and extending from the cuff and forming parts of the joints 16, 16, as will be hereinafter further described. The support members may comprise individual support struts secured to the cuffs by suitable fasteners, such as rivets or screws, or, as shown, the support members may comprise integral extensions of the molded cuffs.

The upper limb support 12 includes an intimately fitted thigh cuff 18, preferably custom molded from polypropylene, for encompassing the wearer's thigh and which is reinforced by a corrugation 20 and entered through the front. The front opening in the cuff is closed around the wearer's thigh with a semi-flexible tongue 22 secured by releasable straps 24, 24 which may be made from Velcro, for example, and which are attached to the cuff at one side of the opening and pass through loops 26, 26 at the other side of the opening. The upper support members, designated by the numerals 28, 28, comprise integral extensions of the thigh cuff 18 and form parts of the orthotic knee joint assemblies 16, 16, hereinafter more fully described.

The lower limb support 14, which provides support for the wearer's calf and foot is also entered through a front opening and includes a calf cuff 30, preferably custom molded from polypropylene, which is closed around the wearer's calf by a semi-flexible tongue 32 secured by a releasable strap 34 and a loop 36. The limb support 14 further includes lower support members 38, 38 which comprise integral upward extensions of the calf cuff 30, and which form parts of the knee joint assemblies 16, 16.

Figure 6:
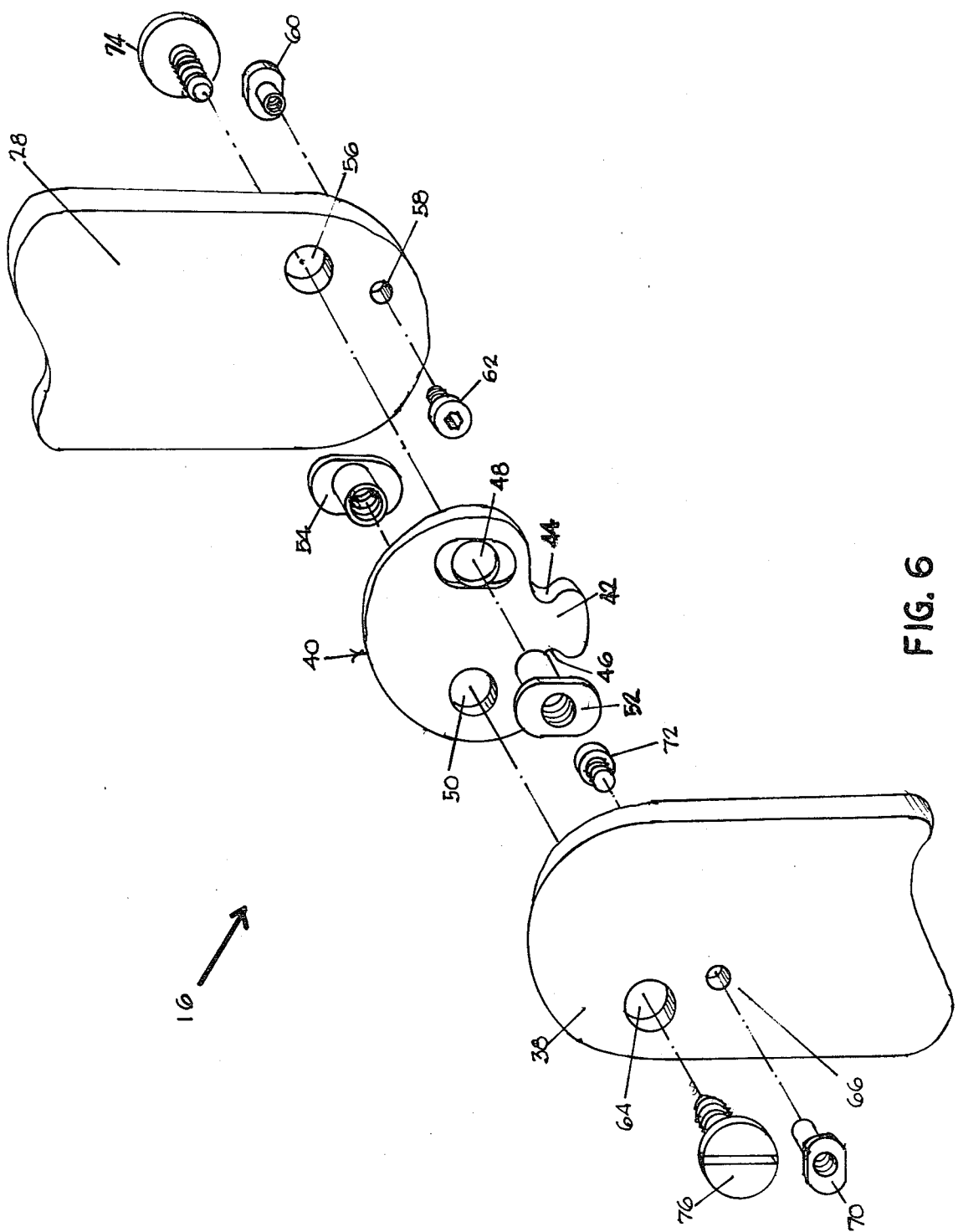
FIG. 6 is a somewhat further enlarged exploded perspective view of the joint assembly shown in FIGS. 2-5.

Considering now a typical joint assembly 16, referring to FIGS. 2-6 and particularly to FIG. 6, the illustrated joint assembly 16 is formed by generally overlapping and laterally spaced apart associated end portions of an upper support member 28, and a lower support member 38. An intermediate member indicated generally at 40 is disposed in the space between the end portions of the associated support members. In accordance with the present invention, either support member may form the inner part of the joint, that is the part proximate the wearer's leg. In the illustrated embodiment 10, the inner part of each joint 16 is formed by an upper support member 28.

The intermediate member 40 comprises a parti-circular disc-like member made from metal, plastic or other material, and has a radially projecting lobe 42 which defines abutment surfaces 44 and 46. A pair of horizontally spaced apart apertures 48 and 50 are formed in the member 40 above the lobe 42 and receive threaded bushings indicated at 52 and 54, respectively, which project from opposite sides of the member 40. Each of the bushings has an enlarged head which is received within an associated shallow complementary recess within the member 40 whereby the bushings 52 and 54 are retained in non-rotatable engagement with the member 40. The upper support member 28 has a cylindrical aperture 56 which receives the projecting end of the bushing 52 therethrough. Another aperture 58 below the aperture 56 receives a threaded sleeve 60 which retains a threaded stop post 62.

The lower support member 38 has a cylindrical aperture 64 which receives the projecting end of the bushing 54. Another aperture 66, below the aperture 64, receives an internally threaded sleeve 70 which retains another threaded stop post 72. Threaded studs 74 and 76 threadably engaged in the bushings 52 and 54, respectively, retain the upper and lower support members 28 and 38 in connected assembly with the intermediate member 40. The bushings 52 and 54 provide parallel first and second pivotal axes for the upper and lower support members 28 and 38, respectively.

Figure 2:
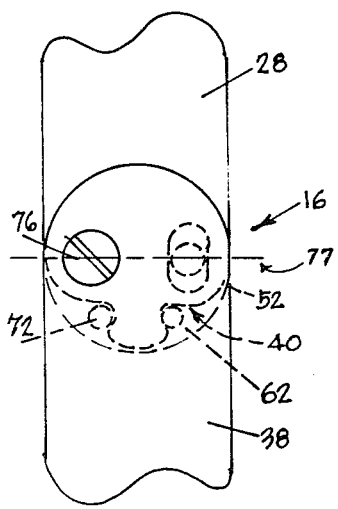
FIG. 2 is a somewhat enlarged fragmentary side elevational view of the limb orthosis shown in FIG. 1 and shows a typical joint assembly.
Figure 3:
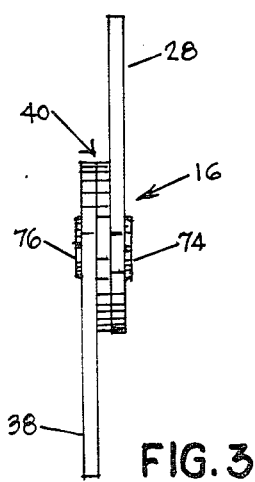
FIG. 3 is a front elevational view of the joint assembly as shown in FIG. 2.

When the joint 16 is in a positin of normal extension, as it appears in FIG. 2, the support members 28 and 38 are longitudinally aligned with each other, the axes of the bushings 52 and 54 are generally transversely spaced apart and the stop posts 62 and 72 are disposed to one side of an axial plane containing the axes of the bushings and indicated by the numeral 77 in FIG. 2.

Figure 4:
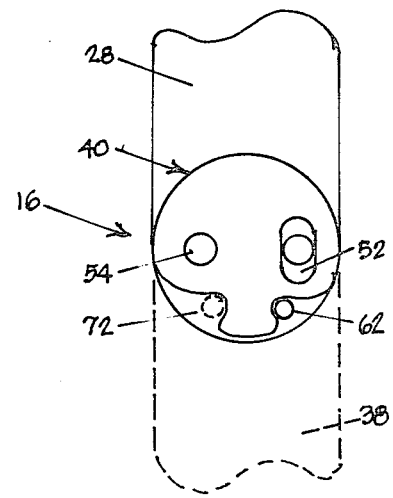
FIG. 4 is similar to FIG. 2 but shows the joint assembly with the lower support member shown in phantom.
Figure 5:
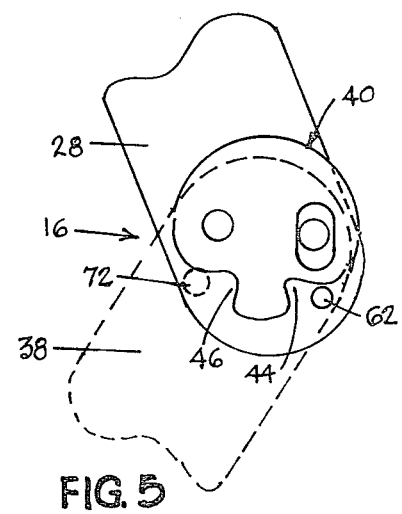
FIG. 5 is similar to FIG. 4 but shows the lower and upper support members in an attitude slightly revolved about their respective axes.

When a limb is supported by the upper and lower limb supports 12 and 14 in a position of normal extension (180 degree angle at the knee) stop post 62 is engaged with abutment surface 44 and stop post 72 is engaged with abutment surface 46, as shown in FIGS. 2 and 4, to prevent the lower support member 38 from pivoting in a counterclockwise direction relative to the upper support member 28, thereby preventing overextension of the anatomical knee supported by the appliance. However, when the limb is placed in an attitude of normal flexion, the stop posts 62 and 72 may be disengaged from the abutment surfaces 44 and 46 allowing the upper support member 28 to pivot in a counterclockwise direction about the axis of the bushing 52 and the lower support member 38 to pivot in a clockwise direction about the axis of the bushing 54 to a position, such as the position shown in FIG. 5. Thus, the illustrated joint assembly 16 can mimic the motions of an associated anatomical joint to permit normal joint flexion while preventing abnormal or overextension of the anatomical joint as in the condition genu recurvatum. All of the motion occurs within a common plane. When two joints, 16, 16 are used, as in the illustrated orthotic appliance 10, shown in FIG. 1, each joint reinforces the other thereby preventing motion in a plane perpendicular to the normal plane of motion, as in the normal action of a healthy knee. Thus, the illustrated joints are effective in control of the conditions genu valgum and genu varum.

The stops, being disposed between and substantially concealed by associated end portions of the upper and lower support members in all normal positions of the joint, do not present exposed pinch points which may be fouled by the wearer's clothing or pinch the wearer's skin. It will now be apparent that the construction of the joint 16 is such that either the upper or the lower support member may comprise the inner part of the joint.

Referring now to FIGS. 7-10, another double-axis knee joint provided with two limiting stops and embodying the present invention is indicated generally at 16a. Parts of the joint 16a which correspond to parts of the joint 16 previously described, bear the same reference numerals as the previously described parts and a letter "a" suffix.

Figure 9:
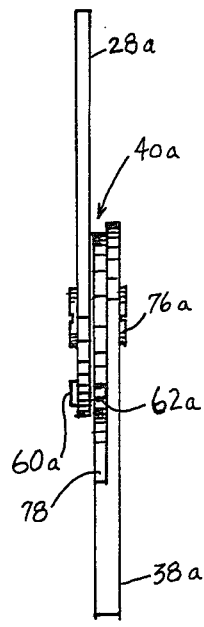
FIG. 9 is a front elevational view of the joint assembly shown in FIG. 7.
Figure 10:
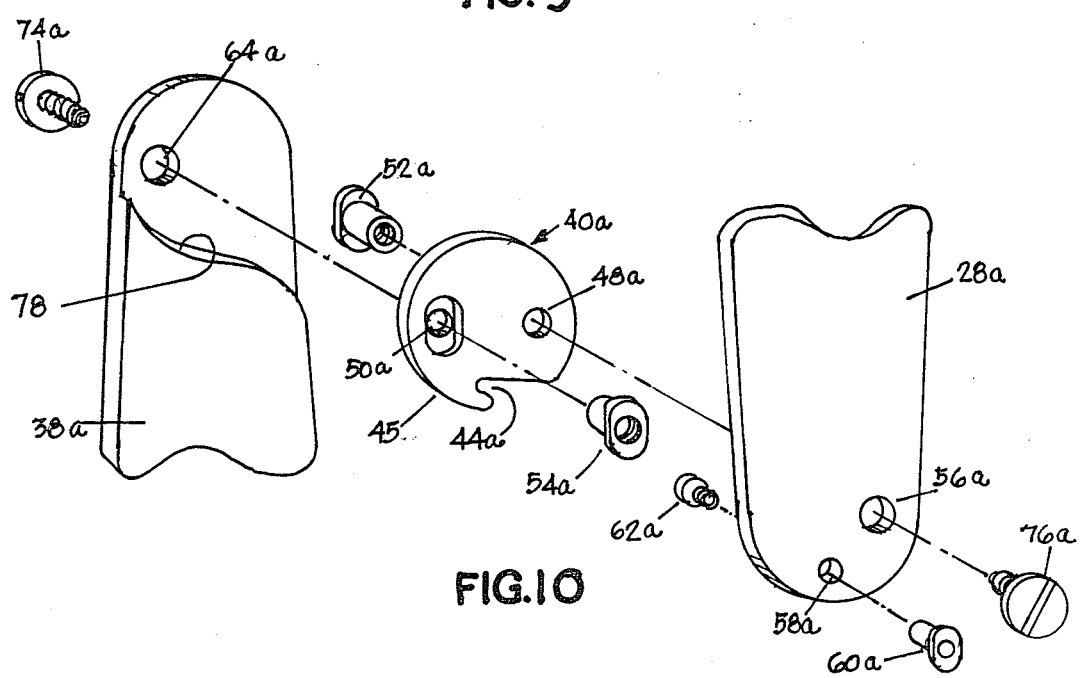
FIG. 10 is an exploded perspective view of the joint assembly shown in FIGS. 7-9.

The joint 16a includes an upper support member 28a, a lower support member 38a, and an intermediate member or parti-circular disc 40a which is disposed generally between and adjacent other surfaces of the upper and lower support members, substantially as shown in FIG. 9. The intermediate member 40a comprises a substantially circular disc which has a diameter slightly less than the width of the associated end portions of the upper and lower support members. Diametrically opposed cylindrical apertures 48a and 50a are formed in the disc 40a for respectively receiving internally threaded bushings 52a and 54a substantially as aforedescribed. An abutment surface 44a is formed on the intermediate member 40a below the apertures 48a and 50a. Another abutment surface 45 is defined by a peripheral edge portion of the disc 40a substantially as shown in FIG. 10.

The upper support member 28a is generally similar to the support member 28 previously described and is provided with apertures 56a and 58a which respectively receives the bushing 52a and a threaded sleeve 60a which retains a stop post 62a. However, the lower support member 38a differs substantially from the support member 38 previously described. Specifically, the support member 38a is relieved at its end portion to define a recess for receiving the intermediate member or disc 40a. The lower portion of the recess is defined by a arcuate abutment surface 78. A cylindrical aperture 64a formed in the end portion of the lower support member receives the projecting end portion of the bushing 54a. Stud fasteners 74a and 76a threaded into the bushings 52a and 54a, respectively, retain the upper and lower support members in assembled relation with the intermediate member 40a.

Figure 7:
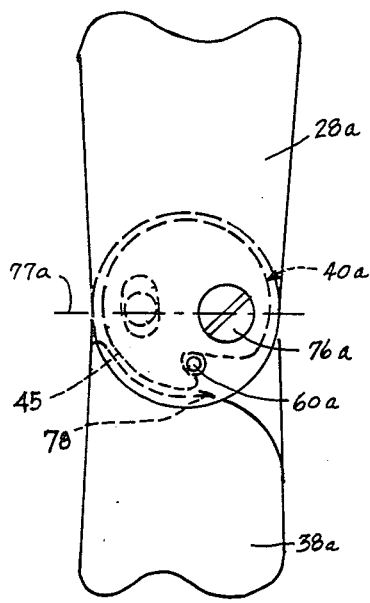
FIG. 7 is similar to FIG. 2 but shows another joint assembly embodiment of the invention.
Figure 8:
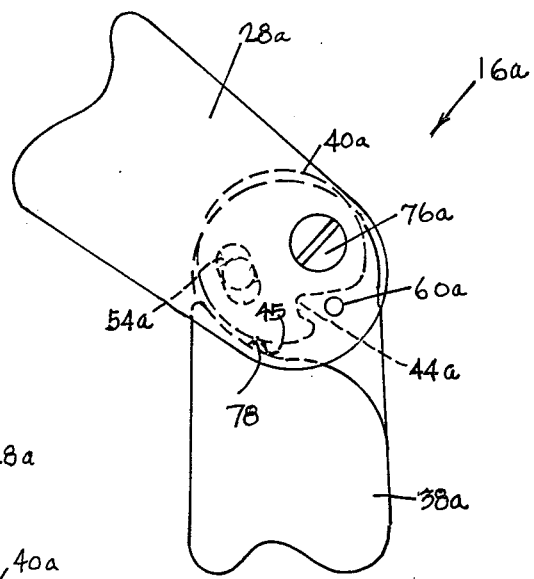
FIG. 8 is a view similar to FIG. 7 but shows the joint assembly in a slightly flexed condition.

When an orthotic appliance, such as the appliance 10 is fitted with joints, such as the joint 16a and a wearer's limb is in an normally extended position the upper and lower support members are substantially longitudinally aligned, as shown in FIG. 7. The stop post 62a is engaged with the abutment surface 44a and the stop surface 45 is engaged with the abutment surface 78. The stop post and abutment surfaces effectively prevent counterclockwise rotation of the lower support member 38 relative to the upper support member 28a from the longitudinally aligned position shown in FIG. 7 thereby preventing overextension of the associated anatomical knee joint. Normal flexion of the knee joint may cause clockwise rotation of the intermediate member 40a about the axis of the bushing 52a and relative to the upper support member 28a. Clockwise rotation of the lower support member 38a about the axis of the bushing 54a and relative to the intermediate member 40a may also occur. This compound motion permits the mechanical joint 16a to substantially mimic the motion of the anatomical knee joint which it supports thereby permitting normal flexion of the knee while preventing abnormal flexion or overextension of the anatomical joint. The abutment surfaces which comprise the stops are substantially disposed between the upper and lower support members and do not present exposed pinch points under normal conditions of knee flexion.

I claim:

1. An orthotic/prosthetic joint assembly comprising longitudinally elongated first and second support members having generally overlapping laterally spaced apart end portions, an intermediate member disposed in the space between said end portions, first connecting means securing the end portion of said first support member to said intermediate member for pivotal movement relative to said intermediate member about a first axis in one direction from a first position of said first support member relative to said intermediate member, second connecting means securing the end portion of said second support member to said intermediate member for pivotal movement relative to said intermediate member about a second axis parallel to said first axis and in a direction opposite said one direction from a first position of said second support member relative to said intermediate member, said joint assembly having a position of normal extension wherein said first and second support members are generally longitudinally aligned with each other and said first and second axes are generally transversely spaced apart, first stop means disposed in said space between said end portion of said support members for preventing pivotal movement of said first support member in said opposite direction from its said first position, and second stop means disposed in said space between said end portions of said support members for preventing pivotal movement of said second support member in said one direction from its said first position, said first and second stop means being disposed between and substantially covered by said first and second end portions in all angular positions of said first and second support members relative to each other.

2. An orthotic/prosthetic joint assembly as set forth in claim 1 wherein said first stop means comprises a first abutment on said intermediate member and a first stop carried by said first support member and engageable with said first abutment.

3. An orthotic/prosthetic joint assembly as set forth in claim 2 wherein said second stop means comprises a second abutment on said intermediate member and a second stop carried by said second support member and engageable with said second abutment.

4. An orthotic/prosthetic joint assembly as set forth in claim 3 wherein said intermediate member has a projecting lobe and said first and second abutments comprise abutment surfaces defined by said lobe.

5. An orthotic/prosthetic joint assembly as set forth in either claim 1 or claim 2 wherein said second stop means comprises coengageable abutment surfaces on said intermediate member and said second support member.

6. An orthotic/prosthetic joint assembly as set forth in claim 5 wherein said second support member has a recess receiving said intermediate member and one of said abutment surfaces is defined by a wall of said recess.

7. An orthotic/prosthetic joint assembly as set forth in claim 5 wherein said intermediate member comprises a parti-circular disc and said first and second axes are eccentric relative to the center of said disc.

8. An orthotic/prosthetic joint assembly as set forth in claim 7 wherein said first and second axes are disposed in a diametric plane of said disc and said first and second stop means are located to one side of said diametric plane.

9. An orthotic/prosthetic joint assembly as set forth in any one of claims 1 through 4 wherein said first and second stop members are disposed to one side of a plane defined by said first and second axes.

10. An orthotic/prosthetic joint assembly as set forth in any one of claims 1 through 4 wherein said first and second connecting means comprise bushings carried by said intermediate member and defining said first and second pivot axes.

11. An orthotic/prosthetic joint assembly comprising a longitudinally elongated first support member having a first end portion, a longitudinally elongated second support member having a second end portion disposed in generally overlapping and laterally spaced relation to said first end portion, an intermediate disc having a parti-circular portion and a generally radially extending lobe portion and disposed in the space between and generally adjacent said first end portion and said second end portion, a first pivot member connecting said first end portion to said intermediate disc for pivotal movement about a first axis parallel to the central axis of said disc and in one direction from a first position of said first support member relative to said disc, a second pivot member connecting said second end portion to said intermediate disc for pivotal movement about a second axis parallel to said central axis and in a direction opposite said one direction from a first position of said second support member relative to said disc, first stop means for preventing pivotal movement of said first support member in said opposite direction from its first position relative to said disc and including a first stop member carried by said first support member and projecting therefrom into said space and engaging one side of said lobe when said first support member is in its first position, and second stop means for preventing pivotal movement of said second support member in said one direction from its first position relative to said disc and including a second stop member carried by said second support member and projecting therefrom into said space and engaging the side of said lobe opposite said one side when said second support member is in its first position, said first and second stop members and said lobe being substantially concealed between and by said first and second end portions in all angular positions of said joint assembly.

12. An orthotic/prosthetic joint assembly as set forth in claim 11 wherein said first and second axes are disposed in a diametric plane of said disc and said lobe is located to one side of said diametric plane.

13. An orthotic/prosthetic joint assembly comprising a longitudinally elongated first support member having a first end portion, a longitudinally elongated second support member including a second end portion and having a recess therein, said first and second end portions being disposed in generally overlapping and laterally spaced relation to each other, an intermediate disc disposed in the space between and generally adjacent said first and second end portions, a first pivot member connecting said first end portion to said intermediate disc for pivotal movement about a first axis parallel to the central axis of the disc and in one direction from a first position of said first support member relative to said disc, a second pivot member connecting said second end portion to said intermediate disc for pivotal movement about a second axis parallel to said central axis and in a direction opposite said one direction from a first position of said second support member relative to said disc, first stop means for preventing pivotal movement of said first support member about said first axis and in said opposite direction from its first position relative to said disc, second stop means for preventing pivotal movement about said second axis and of said second support member in said one direction from its first position relative to said disc and including a peripheral portion of said disc for engaging a wall of said recess when said second support member is in its first position, said first and second stop means being substantially concealed by and between said first and second end portions in all angular positions of said joint assembly.

14. An orthotic/prosthetic joint assembly as set forth in claim 13 wherein said first stop means comprises a stop member carried by said first support member and projecting into said space and an abutment on said disc engaged by said stop member when said first support member is in its first position.

* * * * *